US006789040B2

(12) United States Patent
Kaushikkar

(10) Patent No.: US 6,789,040 B2
(45) Date of Patent: Sep. 7, 2004

(54) SYSTEM, METHOD, AND COMPUTER SOFTWARE PRODUCT FOR SPECIFYING A SCANNING AREA OF A SUBSTRATE

(75) Inventor: Shantanu V. Kaushikkar, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 250 days.

(21) Appl. No.: 09/682,074

(22) Filed: Jul. 17, 2001

(65) Prior Publication Data

US 2002/0024026 A1 Feb. 28, 2002

Related U.S. Application Data

(60) Provisional application No. 60/226,999, filed on Aug. 22, 2000, and provisional application No. 60/286,578, filed on Apr. 26, 2001.

(51) Int. Cl.[7] .......................... G01C 17/00; G01C 19/00
(52) U.S. Cl. ...................................................... 702/150
(58) Field of Search ................................ 702/150, 151, 702/152, 127, 19

(56) References Cited

U.S. PATENT DOCUMENTS

| | | | | | |
|---|---|---|---|---|---|
| 5,593,839 | A | * | 1/1997 | Hubbell et al. | 435/6 |
| 5,856,101 | A | * | 1/1999 | Hubbell et al. | 435/6 |
| 5,874,219 | A | * | 2/1999 | Rava et al. | 435/6 |
| 5,925,525 | A | * | 7/1999 | Fodor et al. | 435/6 |
| 6,090,555 | A | | 7/2000 | Fiekowsky et al. | |
| 6,151,123 | A | * | 11/2000 | Nielsen | 356/445 |
| 6,284,465 | B1 | * | 9/2001 | Wolber | 435/6 |
| 6,287,880 | B1 | * | 9/2001 | Erickson et al. | 438/17 |
| 6,349,144 | B1 | | 2/2002 | Shams | |
| 6,362,004 | B1 | * | 3/2002 | Noblett | 436/43 |
| 6,407,858 | B1 | * | 6/2002 | Montagu | 359/391 |
| 6,466,309 | B1 | * | 10/2002 | Kossakovski et al. | 356/73 |
| 6,469,513 | B1 | * | 10/2002 | Tse | 324/455 |
| 6,567,163 | B1 | * | 5/2003 | Sandstrom | 356/317 |
| 6,587,579 | B1 | * | 7/2003 | Bass | 382/141 |
| 2002/0047853 | A1 | | 4/2002 | Bartell | |

OTHER PUBLICATIONS

Axon Instruments, Inc. Press Release dated Mar. 8, 2000 entitled, "Axon Instruments Announces Release of GenePix Pro 3.0", http://www.axon.com/press/pr20000308.htm.
GenePix Pro 3.0 Software, http://www.apbiotech.com/application/miroarray/GenePix_Pro3.htm.

* cited by examiner

Primary Examiner—John Barlow
Assistant Examiner—Demetrius R. Pretlow
(74) Attorney, Agent, or Firm—William R McCarthy, III; Philip L. McGarrigle; Alan B. Sherr

(57) ABSTRACT

Systems, methods, and computer program products are described for specifying a scanning area of a substrate. In accordance with one method, steps include receiving location data corresponding to a plurality of probe-feature locations on the substrate, storing the location data, accessing the location data, and scanning the substrate based on the accessed location data. A scanning system is described that includes a computer, a scanner, and a computer program product. The product, when executed on the computer, accesses location data corresponding to a plurality of probe-feature locations on a substrate, and controls the scanner's scanning of the substrate based on the accessed location data.

23 Claims, 11 Drawing Sheets

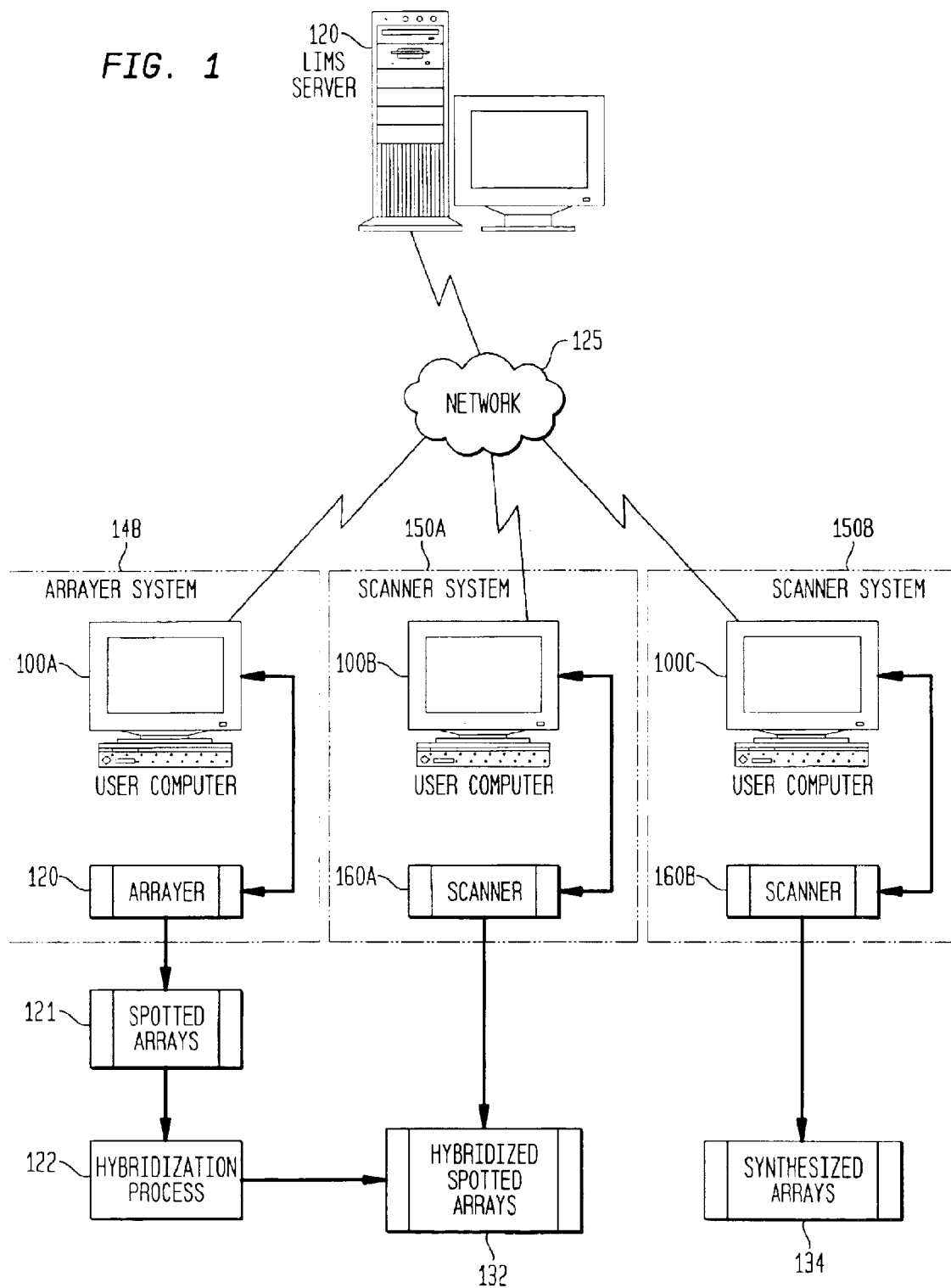

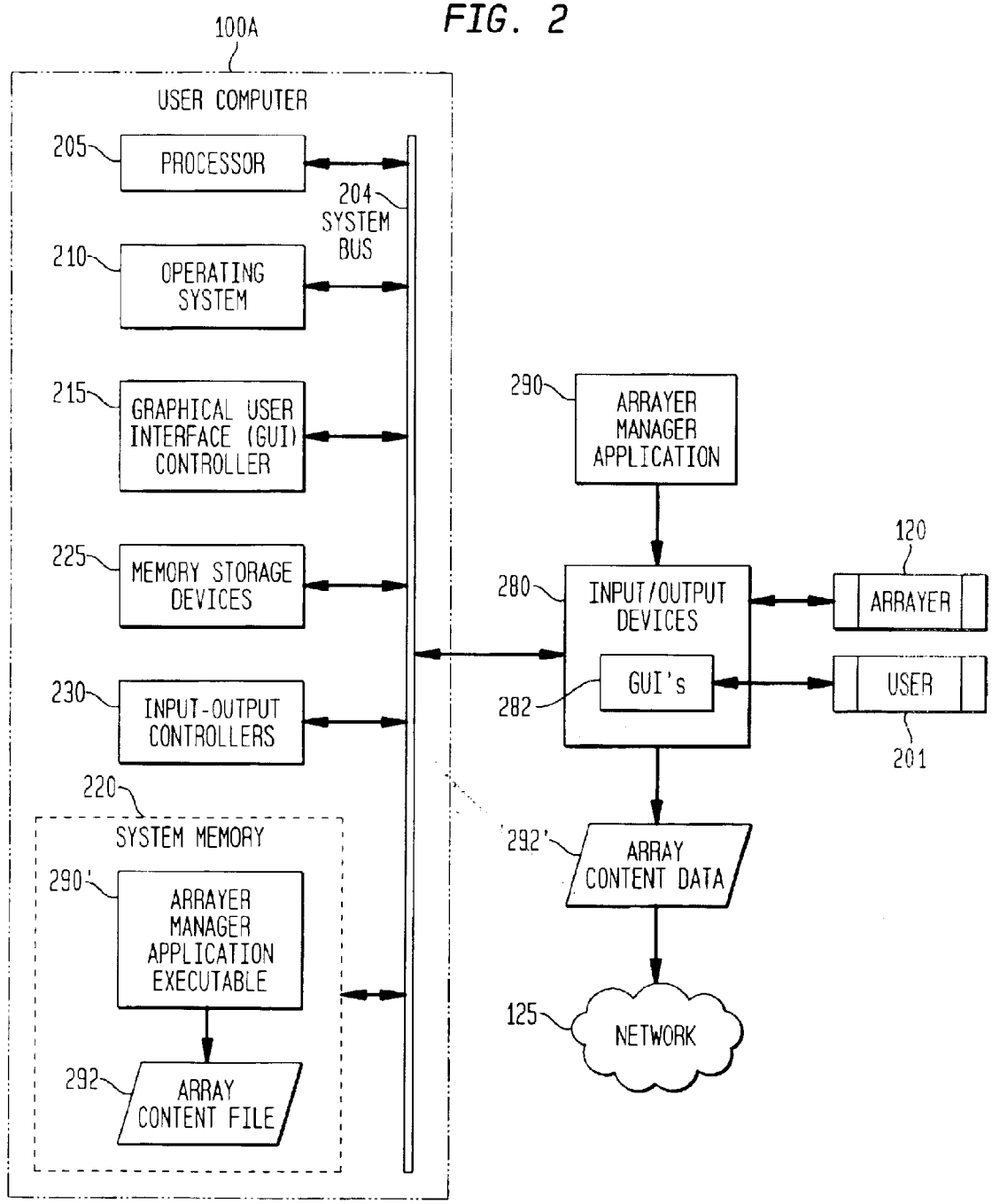

SYSTEM, METHOD, AND COMPUTER SOFTWARE PRODUCT FOR SPECIFYING A SCANNING AREA OF A SUBSTRATE

CROSS REFERENCE TO RELATED APPLICATIONS

The present application relates to and claims priority from U.S. Provisional Patent Application Serial No. 60/226,999, titled "System, Method, and Product for Linked Window Interface," filed Aug. 22, 2000, and U.S. Provisional Patent Application Serial No. 60/286,578, titled "System, Method, and Product for Scanning of Biological Materials," filed Apr. 26, 2001, which are hereby incorporated herein by reference in their entireties for all purposes. The present application also relates to U.S. Patent application Ser. No. 09/682,071 entitled System, Method, and Computer Program Product for Gain Adjustment in Biological Microarray Scanner, and to U.S. Patent application Ser. No. 09/682,076 entitled System, Method, and Computer Software Product for Grid Alignment of Multiple Scanned Images, both of which are filed concurrently herewith and are hereby incorporated herein by reference in their entireties for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF INVENTION

1. Field of the Invention

The present invention relates to systems, methods, and products for making and scanning arrays of biological materials.

2. Related Art

Synthesized probe arrays, such as Affymetrix® GeneChip® arrays, have been used to generate unprecedented amounts of information about biological systems. For example, a commercially available GeneChip® array set from Affymetrix, Inc. of Santa Clara, Calif., is capable of monitoring the expression levels of approximately 6,500 murine genes and expressed sequence tags (EST's). Experimenters can quickly design follow-on experiments with respect to genes, EST's, or other biological materials of interest by, for example, producing in their own laboratories microscope slides containing dense arrays of probes using the Affymetrix® 417™ Arrayer or other spotting devices.

Analysis of data from experiments with synthesized and/or spotted probe arrays may lead to the development of new drugs and new diagnostic tools. In some conventional applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner from Affymetrix, Inc. of Santa Clara, Calif.

There is a great demand in the art for methods for organizing, accessing and analyzing the vast amount of information collected by scanning microarrays. Computer-based systems and methods have been developed to assist a user to obtain and visualize the vast amounts of information generated by the scanners. These commercial and academic software applications typically provide such information as intensities of hybridization reactions or comparisons of hybridization reactions. This information may be displayed to a user in graphical form.

SUMMARY OF INVENTION

In accordance with some embodiments of the present invention, a computer program product is described that includes an arrayer manager application and a scanner control application. The arrayer manager application receives and stores location data corresponding to a plurality of probe-feature locations on a substrate. The scanner control application accesses the location data and causes scanning of the substrate based, at least in part, on the accessed location data.

In some implementations, the arrayer manager application and the scanner control application may be separate computer programs, and they may be executed on separate computers. For example, the arrayer manager application may be executed on a first computer that controls an arrayer, and the scanner control application may be executed on a second computer that controls a scanner.

One advantage provided by the computer program product, whether executed on separate computers or a same computer, is that a user wishing to scan a probe array need not provide information regarding the locations of probes on the array's substrate. Rather, the scanner user simply specifies or selects a file or other data storage structure in which the location data has been stored. The user need not be the same user that caused the location data to be stored by specifying probe-feature locations on the substrate. Thus, for example, the scanner user need not be familiar with, or have knowledge of, the scheme for arraying probes on the substrate as determined by the arrayer user. One scanner user may scan arrays prepared by numerous array users. More generally, the arraying and scanning operations may occur at separate places and times as well as involve separate personnel. This flexibility generally simplifies the scanning operation and reduces the possibilities of error in determining appropriate scanning areas on substrates.

In one embodiment, a computer program product is described that includes a user-interface manager. The user interface manager enables user specification of a plurality of probe-feature locations on a substrate, and provides location data corresponding to the probe-feature locations. The computer program product also includes a data storage manager that stores the location data in a memory unit. Yet another element of the product is an output manager enabled to provide the location data to a scanner control application. This scanner control application causes scanning of the substrate based, at least in part, on the accessed location data. The user interface manager may enable user specification of the probe-feature locations by specifying one or more spacing distances between probe features, by specifying one or more patterns of probe feature locations, and/or by specifying coordinates. The coordinates may include x and y coordinates.

In other embodiments, a computer program product is described that includes a data retriever that accesses location data corresponding to a plurality of probe-feature locations on a substrate. The product also has a scan-area controller that controls scanning of the substrate based, at least in part, on the accessed location data. This location data is stored in a memory unit of a first computer that, in some implementations, controls an arrayer. The data retriever may provide a user interface that enables user selection of the location data, and may access the location data based, at least in part, on the user selection. The data retriever may receive the location data from the first computer and store the location data in a memory unit of a second computer, which may control a scanner. In Some implementations, the probe-feature locations include locations of probes of a spotted array, or of a synthesized array.

In further embodiments, a method is described that includes (a) receiving location data corresponding to a plurality of probe-feature locations on a substrate; (b) storing the location data; (c) accessing the location data; and (d) scanning the substrate based, at least in part, on the accessed location data. Step (a) may include providing a first user interface that enables user specification of the probe feature locations. Step (c) may include (i) providing a second user interface that enables user selection of the location data; and (ii) accessing the location data based, at least in part, on the user selection. In some implementations, step (b) includes storing the location data in an array content file in a memory unit of a first computer, which may control an arrayer. Step (c) in these implementations may include (i) transferring the location data from the first computer to a memory unit of a second computer; (ii) providing a second user interface that enables user selection of the location data; and (iii) accessing the location data from the memory unit of the second computer based, at least in part, on the user selection. The second computer may control a scanner.

Another described embodiment is a method including (a) accessing location data corresponding to a plurality of probe-feature locations on a substrate, wherein the location data is stored in a memory unit of a computer; and (b) scanning the substrate based, at least in part, on the accessed location data.

A further embodiment is a scanning system that includes a scanner and a computer program product. The product has a data retriever that accesses location data corresponding to a plurality of probe-feature locations on a substrate, and a scan-area controller that controls scanning by the scanner of the substrate based, at least in part, on the accessed location data.

Yet a further embodiment is a scanning system having a computer, a scanner, and a computer program product. The product, when executed on the computer, performs a method including accessing location data corresponding to a plurality of probe-feature locations on a substrate, and controlling scanning by the scanner of the substrate based, at least in part, on the accessed location data.

The above embodiments and implementations are not necessarily inclusive or exclusive of each other and may be combined in any manner that is non-conflicting and otherwise possible, whether they be presented in association with a same, or a different, aspect of the invention. The description of one embodiment or implementation is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments and implementations are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost one or two digits of a reference numeral indicates the number of the figure in which the referenced element first appears (for example, the element 125 appears first in FIG. 1, the element 1010 first appears in FIG. 11). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

FIG. 1 is a simplified schematic diagram of one embodiment of networked systems for generating, sharing, and processing probe array data among computers on a network, including an arrayer system for generating spotted probe arrays and scanner systems for scanning spotted and synthesized probe arrays;

FIG. 2 is a functional block diagram of one embodiment of a user computer of the networked computers of FIG. 1 suitable for controlling the arrayer of FIG. 1 to produce spotted arrays;

DETAILED DESCRIPTION

Figure 3A:
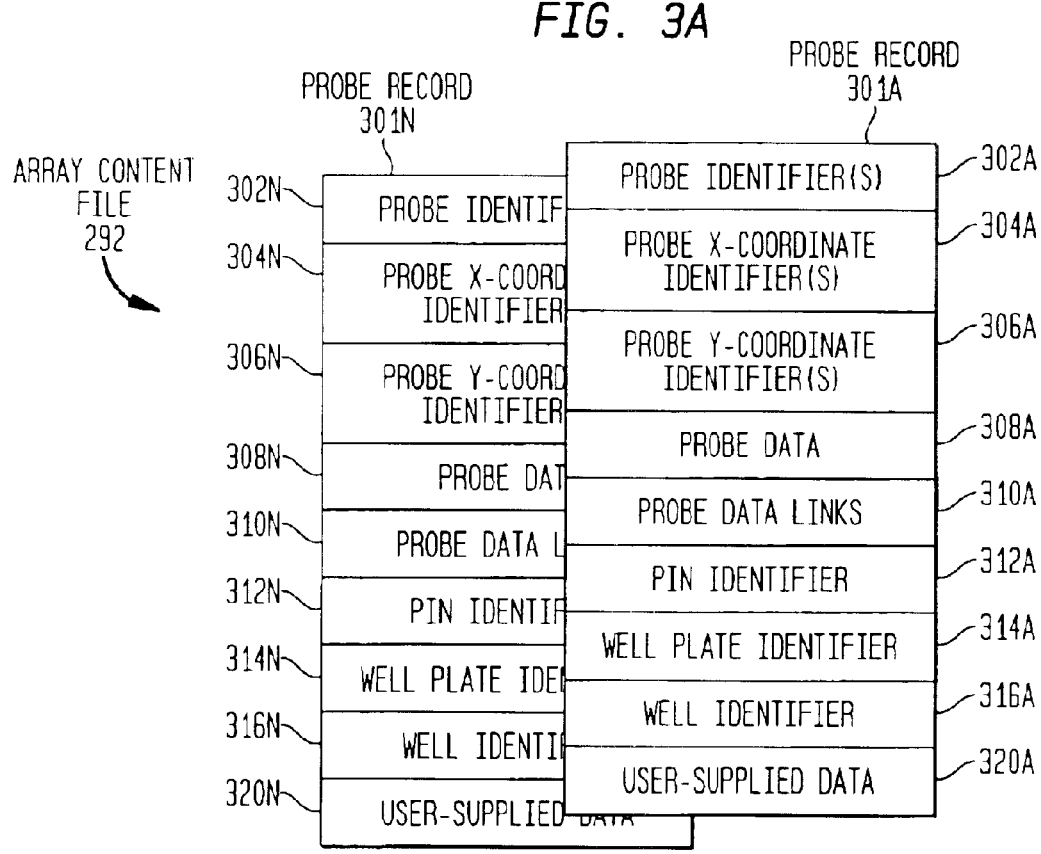
FIG. 3A is a graphical representation of data records in one embodiment of a data file suitable for storing data regarding spotted arrays produced in cooperation with the user computer of FIG. 2 and the arrayer of FIG. 1.

Systems, methods, and software products to acquire, process, analyze, and/or display data from experiments with synthesized and/or spotted arrays are described herein with respect to illustrative, non-limiting, implementations. Various other alternatives, modifications and equivalents are possible. For example, while certain systems, methods, and computer software products are described using exemplary embodiments with reference to spotted arrays analyzed using Affymetrix scanners and/or Affymetrix software, the systems, methods, and products of the present invention are not so limited. For example, they generally may be applied with respect to many other probe arrays, including many types of parallel biological assays.

Probe Arrays

For example, certain systems, methods, and computer software products are described herein using exemplary implementations for acquiring, analyzing, and/or displaying data from arrays of biological materials produced by the Affymetrix® 417™ or 427™ Arrayer. Other illustrative implementations are referred to in relation to data from experiments with Affymetrix® GeneChip® arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, aspects of the systems, methods, and products described herein may, in some implementations, be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates, supports, or media (all or any of which may hereafter generally and collectively be referred to as substrates). Some implementations of synthesized arrays, their preparation, substrates, and the like are described in U.S. Pat. Nos. 5,744,305 and 5,445,934, which are hereby incorporated herein by reference in their entireties for all purposes. Moreover, with respect to some implementations in which the context so indicates or allows, the probes need not be immobilized in or on a substrate, and, if immobilized, need not be disposed in regular patterns or arrays. For convenience, the term probe array will generally be used broadly hereafter to refer to all of these types of arrays and parallel biological assays.

For convenience, an array made by depositing or positioning pre-synthesized or pre-selected probes on a substrate, or by depositing/positioning techniques that may be developed in the future, is hereafter referred to as a spotted array. Typically, but not necessarily, spotted arrays are commercially fabricated on microscope slides. These arrays often consist of liquid spots containing biological material of potentially varying compositions and concentrations. For instance, a spot in the array may include a few strands of short polymers, such as oligonucleotides in a water solution, or it may include a high concentration of long strands of polymers, such as complex proteins. The Affymetrix® 417™ and 427™ Arrayers, noted above, are devices that deposit densely packed arrays of biological material on a microscope slide in accordance with these techniques. Aspects of these, and other, spot arrayers are described in U.S. Pat. Nos. 6,121,048, 6,040,193 and 6,136,269, in PCT Applications Nos. PCT/US99/00730 (International Publication Number WO99/36760) and PCT/US 01/04285, in U.S. patent application Ser. Nos. 09/122,216, 09/501,099, and 09/862,177, and in U.S. Provisional Patent Application Serial No. 60/288,403, all of which are hereby incorporated by reference in their entireties for all purposes. Other techniques for depositing or positioning biological probes on a substrate, i.e., creating spotted arrays, also exist. For example, U.S. Pat. No. 6,040,193 to Winkler, et al. is directed to processes for dispensing drops of biological material. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Other techniques for producing spotted arrays are based on ejecting jets of biological material. Some implementations of the jetting technique use devices such as syringes or piezo electric pumps to propel the biological material.

Spotted arrays typically are used in conjunction with tagged biological samples such as cells, proteins, genes or EST's, other DNA sequences, or other biological elements. These samples, referred to herein as targets, typically are processed so that they are spatially associated with certain probes in the probe array. In one non-limiting implementation, for example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets' complementary probes. The associated probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term probe as used herein, it is noted that contradictory conventions exist in the relevant literature. The word probe is used in some contexts to refer not to the biological material that is deposited on a substrate, as described above, but to what has been referred to herein as the target. To avoid confusion, the term probe is used herein to refer to compounds such as those deposited on a substrate to create spotted arrays.

FIG. 1 is a simplified schematic diagram of illustrative systems for generating, sharing, and processing data derived from experiments using probe arrays (i.e., spotted arrays and/or synthesized arrays). More particularly, an illustrative arrayer system 148 and illustrative scanner systems 150A and 150B (collectively, scanner systems 150) are shown. In this example, data may be communicated among user computer 100A of system 148, user computers 100B and 100C of systems 150, and Laboratory Information Management (LIMS) server 120 over network 125. LIMS server 120 and associated software generally provides data capturing, tracking, and analysis functions from a centralized infrastructure. Aspects of a LIMS are described in U.S. Provisional Patent Application Nos. 60/220,587 and 60/273,231, both of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 100A and 100B to operate and process data from an arrayer and scanner, respectively, as in the illustrated implementation, a single computer may be used for all of these purposes in other implementations. More generally, a large variety of computer and/or network architectures and designs may be employed, and it will be understood by those of ordinary skill in the relevant art that many components of typical computer network systems are not shown in FIG. 1 for sake of clarity.

Arrayer 120

The illustrative system of FIG. 1 includes an arrayer 120 for producing spotted arrays, such as represented by spotted arrays 121. For example, arrayer 120 may be the Affymetrix® 417™ or 427™ Arrayer (commercially available from Affymetrix, Inc. of Santa Clara, Calif.), elements of which are hereafter described to provide an example of how arrayer 120 may operate in a commercial embodiment. As noted above, however, numerous variations are possible in the technologies and structures that may be used to produce spotted arrays, and thus it will be understood that the following description of arrayer 120 is merely illustrative, and is non-limiting.

Arrayer 120 of the illustrated implementation deposits spots on substrates consisting of standard glass microscope slides. The slides are held on a flat platen or cartridge (not shown) that registers the slides relative to a printing head (not shown) that is lowered and raised to effect spotting. The spotting elements of the printing head may include, for example, various numbers of Affymetrix® Pin-and-Ring™ mechanisms, as described, e.g., in U.S. patent application Ser. No. 09/862,177, or U.S. Provisional Patent Application Serial No. 60/288,403, incorporated by reference above. For example, the printing head in illustrative implementations may accommodate 1, 4, 8, 12, 32 or 48 pairs of pin and ring elements to deposit the spots of biological material onto the slide. Arrayer 120 thus may in some implementations be capable of rapidly depositing many spots of biological fluids, such as would be useful in preparing large numbers of DNA microarrays. The ring of the Pin-and-Ring™ mechanism in one implementation includes a circular ring section formed from a circular piece of metal. The ring is attached at the end of an arm section that extends from a cylinder. The pin in this example is a single, rod-like device having at one end a very narrow tip. During operation, the pin is inserted into and through the cylinder with the tip being capable of moving freely through the opening of the ring.

In some implementations, fluids to be spotted onto the microscope slides may be stored in and retrieved from well plates (also commonly referred to as microtiter plates) having, for example a standard number of 96 or 348 wells. The well plates loaded with fluids may, in some implementations, be inserted by a user into a carousel included in arrayer 120. Arrayer 120 may include a robotic system having an effector arm that, under computer control, may be instructed to retrieve a well plate from the carousel. Arrayer 120 may, in some implementations, be capable of automatically identifying well plates. For example, machine readable indicators, e.g., bar codes, may be attached to the well plates and a bar code reader may be attached to the robotic system for reading the bar codes. The robotic system pivots the retrieved well plate from the carousel to a well plate retainer on the platen. In other implementations, a user may manually place slides on the platen.

Arrayer 120 further includes a robotic system that may be instructed, under computer control, to position the printing head with respect to the well plate in the well plate retainer in order to obtain fluids from the well plate for spotting. For example, as described in U.S. patent application Ser. No. 09/862,177, referred to above, rings of the printing head may be lowered into the wells of the well plate while the pins of the printing head remain out of contact with the fluids. The ring section is then raised out of the fluids. Given the design of the rings, an amount of the fluid is retained within the rings by the surface tension of the fluid and the surface activity of the inner walls of the rings. After the rings are raised out of the sample solution, the fluid held in each ring forms a convex meniscus that protrudes from the bottom opening of the ring. The printing head, including the rings with fluids, can then be positioned at a location above a substrate (i.e., microscope slide in this example) onto which a fraction of the fluid in each ring is to be deposited. The fluid volume in the ring is sufficient to deposit or spot more than one fraction. In fact, several hundred to a thousand or more fractions can be deposited from a single fluid volume retained in a ring. The number of fractions will depend on the desired volume of each fraction, the dimensions of the pin and the viscosity of the fluid.

Once the pin and ring mechanism is position over the desired location on the substrate, the tip of the pin is then lowered into, through and out of the fluid retained in the ring. The surface tension of the fluid retains the fluid within the ring while the pin penetrates into and moves through and out of the fluid. A fraction of the fluid is retained on the tip of the pin forming a meniscus. The portion of the pin that passes through the ring has a diameter that typically is small compared to the diameter of the ring, enabling the pin to pierce the fluid without breaking the meniscus and causing the fluid to leave the ring.

The pin with the fluid on the tip is lowered toward the surface of the substrate until the meniscus of the fluid on the end of the pin makes initial contact with the surface of the substrate. During typical operation, the pin contacts the substrate without damaging force. The fluid then adheres via surface tension to the surface of the substrate, and as the pin is raised, the fluid is transferred to the surface of the substrate by surface tension and gravity. The pin is moved back through and above the fluid in the ring. The process of sample deposition can then be repeated by repositioning the pin and ring mechanism at another desired location above the surface of the substrate. Alternatively, the pin and ring can be positioned over another, different surface.

In this exemplary implementation, the printing head is positioned on an x-y gantry that is capable of moving the printing head across the length and width of the platen, and thus over numerous slides retained on the platen. For example, the printing head may move in a serpentine manner from slide to slide along a column of slides arranged on the platen, and then back along an adjacent column of slides on the platen. The movement of the printing head may be controlled in accordance with various techniques such as using sensors to count markers and arrive at a preprogrammed destination. The printing head may optionally be directed under computer control to wash and dry stations to clean the pins and rings between spotting applications.

User Computer 100A

As shown in FIG. 1 and noted above, arrayer 120 operates in the illustrated implementation under computer control, e.g., under the control of user computer 100A. Although computer 100A is shown in FIG. 1 for clarity as being directly coupled to arrayer 120, it may alternatively be coupled to arrayer 120 over a local-area, wide-area, or other network, including an intranet and/or the Internet.

FIG. 2 is a functional block diagram showing an illustrative implementation of computer 100A. Computer 100A may be a personal computer, a workstation, a server, or any other type of computing platform now available or that may be developed in the future. Typically, computer 100A includes known components such as processor (e.g., CPU) 205, operating system 210, system memory 220, memory storage devices 225, graphical user interface (GUI) controller 215, and input-output controllers 230, all of which typically communicate in accordance with known techniques such as via system bus 204. It will be understood by those skilled in the relevant art that there are many possible configurations of the components of computer 100A and that some components that may typically be included in computer 100A are not shown, such as cache memory, a data backup unit, and many other devices.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 230 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. GUI controller 215 may comprise any of a variety of known or future software programs for providing graphical input and output interfaces between computer 100A and a user 201 (e.g., an experimenter wishing to use arrayer 120 to generate spotted arrays), and for processing inputs from user 201 (hereafter sometimes referred to as user inputs or user selections).

Arrayer Manager Application 290

Arrayer manager application 290 of the illustrated implementation is a software application that controls functions of arrayer 120 and processes data supplied by user 201. As more particularly described with respect to certain implementations in U.S. Provisional Patent Application Serial No. 60/288,403, incorporated by reference above, application 290, when executed in coordination with processor 205, operating system 210, and/or GUI controller 215, performs user interface functions, data processing operations, and data transfer and storage operations. For example, with respect to user interface functions, user 201 may employ one or more of GUI's 282 to specify and describe particular clones and their location in particular wells of particular well plates. Using another of GUI's 282, user 201 may specify how spots of the clones are to be arranged in arrays on one or more slides, as described in greater detail below with respect to fields 304 and 306 of array content file 292 shown in FIG. 3A. Yet another of GUI's 282 may be used to operate arrayer 120, e.g., to initiate the spotting of a number of slides without further user participation.

As will be evident to those skilled in the relevant art, application 290 may be loaded into system memory 220 and/or memory storage device 225 through an input device of devices 280. Alternatively, application 290 may be implemented as executable instructions stored in firmware. Executable code corresponding to application 290 is referred to as arrayer manager application executable 290' and is shown for convenience with respect to the illustrated implementation as stored in system memory 220. However, instructions and data including executable instructions of application 290, and data used or generated by it, may be located in or shifted among other memory devices, local or remote, as convenient for data storage, data retrieval, and/or execution.

Figure 3B:
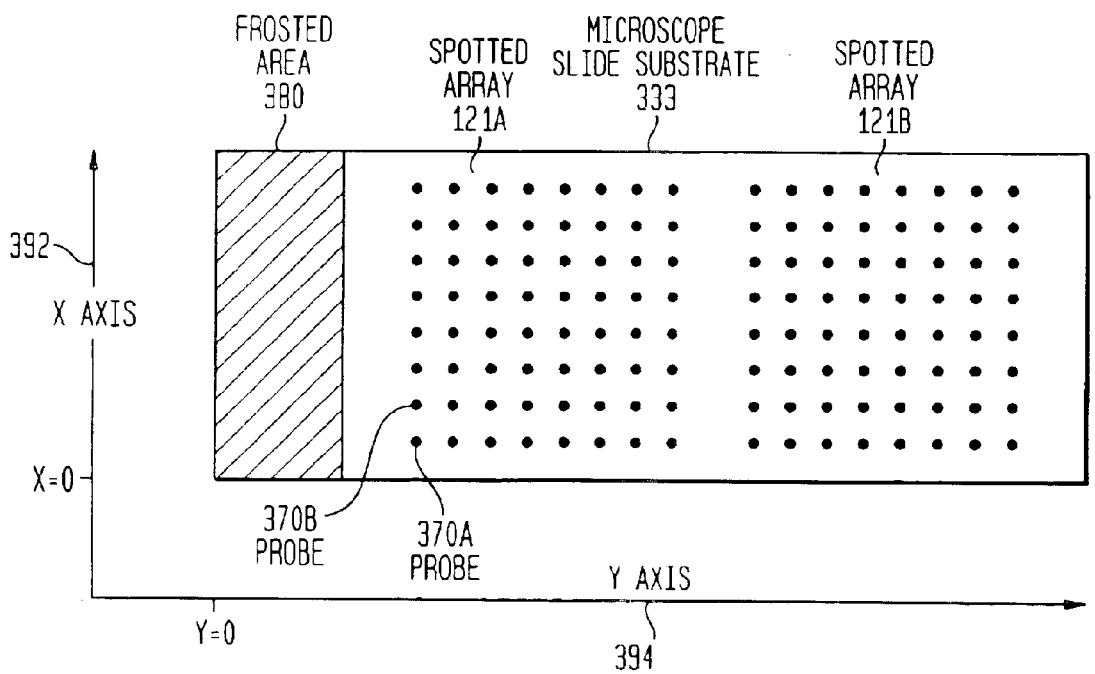
FIG. 3B is a graphical representation of a microscope slide including illustrative embodiments of spotted arrays produced in cooperation with the user computer of FIG. 2 and the arrayer of FIG. 1.

FIG. 3A is a graphical representation of illustrative data records in one implementation of a data file generated by arrayer manager application executable 290'. The data file in this illustration, referred to as array content file 292, consists of records 301, each one of which (i.e., records 301A through 301N for any number of N records) corresponds to one of N spots, i.e., probes, that have been deposited, or are planned to be deposited, on spotted arrays 121. For example, with reference to the graphical representation of spotted arrays 121 shown in FIG. 3B, two arrays 121A and 121B (collectively, arrays 121) have been printed on microscope slide substrate 333 by arrayer 120. Array 121A includes probe 370A. It is assumed for purposes of illustration that data relating to probe 370A is stored by executable 290' in probe record 301A. In this example, each of the records in file 292 includes the following illustrative fields: probe identifier(s) 302, probe x-coordinate identifier(s) 304, probe y-coordinate identifier(s) 306, probe data 308, probe data links 310, pin identifier 312, well plate identifier 316, and user-supplied data 320.

The field in record 301A labeled probe identifier(s) 302A thus, in this example, includes certain information related to the identification of probe 370A. For instance, field 302A may include a name for cDNA deposited by a pin of arrayer 120 in array 121A to produce probe 370A. In various implementations, field 302A may also, or in addition, include a nucleotide identifier and/or a gene symbol that identifies probe 370A. Also, field 302A may include a build or release number of a database so that the data source used to develop the probe can be identified. As yet another example of information that may be included in field 302A, a probe may be identified as either an original or as a replicate. For instance, for quality control or other reasons, probe 370B of array 121A may be the same probe as probe 370A, or a number of such replicate probes may be deposited. The designation of original or replicate number assists in comparing results from probes that are based on the same sample. As one of ordinary skill in the relevant art will readily appreciate, all or some of this identifying data may be stored as a single value in field 302A (such as, for example, concatenating name, nucleotide identifier, etc.), in separate fields (e.g., 302A', 302A'', etc., not shown), in linked fields, and so on as may be convenient for data storage and/or processing. The other fields described below similarly are only representative of many possible storage and data retrieval architectures.

Field 308A, labeled probe data in this example, may include probe-related data such as the chromosome location of the gene or EST represented by the probe, the band location on the chromosome, a SNP or other type of marker that can identify the location on the chromosome, and so on. Field 310A, labeled probe data links in this example, similarly may include an accession number from GenBank, a UniGene cluster number, and/or another identifier that facilitates access to data related to probe 370A that is stored in a database. This database may, but need not, be external to computer 100A and accessed via network 125 and/or the Internet or other network. Systems for providing access to such information are described, for example, in U.S. Provisional Patent Application Serial No. 60/288,429, hereby incorporated herein by reference in its entirety. Field 312A of this example identifies the pin on the print head(s) that is used to deposit probe 370A onto the slide. This information may be useful in comparing probes deposited with the same pin to determine, for example, if the pin is defective. Fields 314A and 316A contain information that respectively identifies the well plate and particular well from which biological fluid was taken to create probe 370A. Field 320A may contain a variety of data supplied by user 201 such as the user's name, the data of the experiment, and so on. It will be understood that there are many other types of data relating to probe 370A that may be stored, and that numerous alternative arrangements may be implemented for storing them.

As will be described below in relation to the operation of scanner 160A, location information is of particular relevance to the scanning of array 121A to detect probe-target pairs. Fields 304A and 306A are used to identify the location of probe 370A on the slide in x and y coordinates, respectively. It will be understood that other coordinate systems (e.g., radial system) could be used, and that the definition of the orientation and zero points of the coordinate references of the present example are illustrative only. In one implementation of the present example, field 304A could include primary and secondary row coordinates, and field 306A could include primary and secondary column coordinates, that identify the position of probe 370A. For instance, arrays 121A and 121B could be viewed as arranged in a single primary column (disposed horizontally in FIG. 3B) in which array 121A occupies the first primary row and array 121B occupies the second primary row. Such an implementation may be said to involve relative, rather than absolute, locations because locations of probes are specified in relation to each other rather than in relation to a reference point on the substrate.

It may be advantageous in some implementations to specify absolute, rather than relative, locations. In one such implementation, orthogonal x and y axes could be defined in relation to the sides of the microscope slide, such as x axis 392 and y axis 394 of the illustrated example, with the 0,0 reference coordinates defined with reference to a particular point on the slide. For instance, some slides are manufactured with a frosted area, such as area 380 of this example, so that a user may more easily label or write on the slide, or for other reasons. A particular point at a corner of the frosted area could readily be defined as the reference coordinate, or any of various other methods could be used to specify a reference coordinate on, or spatially related to, a point on the substrate.

User 201 could thus, using for example one of GUI's 282, specify that the position of probe 370A should be 0.3 millimeters along x axis 392 and 3.0 millimeters along y axis 394. This specification could be accomplished, for example, by specifying where probe 370A is to be located in reference to the reference coordinate. Assuming a spacing between probes of 300 microns, probe 370B of the example illustrated in FIG. 3B would thus be positioned at x, y coordinates of 0.6 millimeters, 3.0 millimeters. In some implementations, user 201 could specify the spacing between probes (e.g., probes are to be located 300 microns from each other in both the x and y directions). In further implementations, user 201 could specify the locations of a subset, or all of, the probes by specifying coordinates of each of the subset, or of all, of the probes in relation to a reference coordinate on the substrate. In yet other non-limiting illustrative implementations, user 201 could specify various probe array patterns such as ones in which a probe array is replicated on a same substrate at a specified x and y distance from the original probe array, or in which the rows or columns of an original and replicate probe array are interleaved with each other. In such implementations, user 201 may hereafter be referred to as specifying one or more patterns of probe feature locations. Various combinations of each of the preceding techniques, and/or others, may also be used.

In some implementations, a printing head of arrayer 120 may include multiple pins, quills, ink-jets, or other elements for depositing probes, and these devices may be positioned at fixed positions with respect to each other. Thus, assuming multiple elements deposit probes at each printing operation, the locations of some probes may be determined in part by the fixed positions rather than solely by the user. In other implementations, such as for example when a single printing element is used or printing element positions are variable, user 201 may have freedom to specify a location for each probe in one or more probe arrays.

Probe location information such as stored in records 304 and 306 of file 292, as well as other information in that file, may be stored, as noted, in system memory 220 of user computer 100A, and may also be shared or distributed among other computers on network 125 or elsewhere. In particular, it is illustratively assumed for purposes of the present examples that the data in file 292, referred to as array content data 292', is transferred over network 125 to user computer 100B, described below.

Scanner 160A: Optics and Detectors

Any of a variety of conventional techniques, or ones to be developed in the future, may be used to generate probe-target pairs in probe arrays that may be detected using a scanner. As one illustrative example that will be familiar to those of ordinary skill in the relevant art, conventional fluidics stations, hybridization chambers, and/or various manual techniques (as, for example, generally and collectively represented by hybridization process 122 in FIG. 1) may be used to apply one or more labeled targets to spotted arrays on microscope slides. In a particular implementation, for instance, sample of a first target may be labeled with a first dye (an example of what may more generally be referred to hereafter as an emission label) that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probes of spotted arrays on microscope slides, and conditions may be created conducive to hybridization reactions, all in accordance with known techniques. In accordance with other techniques, such as typically are applied with respect to Affymetrix® Gene-Chip® synthesized arrays, samples of one labeled target are applied to one array and samples of a second labeled target are applied to a second array having the same probes as the first array. Hybridization techniques are applied to both arrays. For example, synthesized arrays 134 of FIG. 1 may be illustratively assumed to be two GeneChip® synthesized arrays that have been subject to hybridization processes with respect to two different target samples, each labeled with different fluorescent dyes. See, e.g., U.S. Pat. No. 6,114,122, which is hereby incorporated by reference herein in its entirety.

Many scanner designs may be used to provide excitation signals to excite labels on targets or probes, and to detect the emission signals from the excited labels. In references herein to illustrative implementations, the term excitation beam may be used to refer to light beams generated by lasers to provide the excitation signal. However, excitation sources other than lasers may be used in alternative implementations. Thus, the term excitation beam is used broadly herein. The term emission beam also is used broadly herein. As noted, a variety of conventional scanners detect fluorescent or other emissions from labeled target molecules or other material associated with biological probes. Other conventional scanners detect transmitted, reflected, or scattered radiation from such targets. These processes are sometimes generally and collectively referred to hereafter for convenience simply as involving the detection of emission beams. The signals detected from the emission beams are generally referred to hereafter as emission signals and this term is intended to have a broad meaning commensurate with that intended herein for the term emission beams.

Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar devices to register the collected emission beams. For example, a scanning system for use with a fluorescently labeled target is described in U.S. Pat. No. 5,143,854, hereby incorporated by reference in its entirety for all purposes. Other scanners or scanning systems are described in U.S. Pat. Nos. 5,578,832, 5,631,734, 5,834,758, 5,936,324, 5,981,956, 6,025,601, 6,141,096, 6,185,030, 6,201,639, 6,218,803, and 6,252,236; in PCT Application PCT/US99/06097 (published as WO99/47964); in U.S. patent application Ser. No. 09/681,819; and in U.S. Provisional Patent Application Serial No. 60/286,578, each of which also is hereby incorporated herein by reference in its entirety for all purposes.

Figure 4:
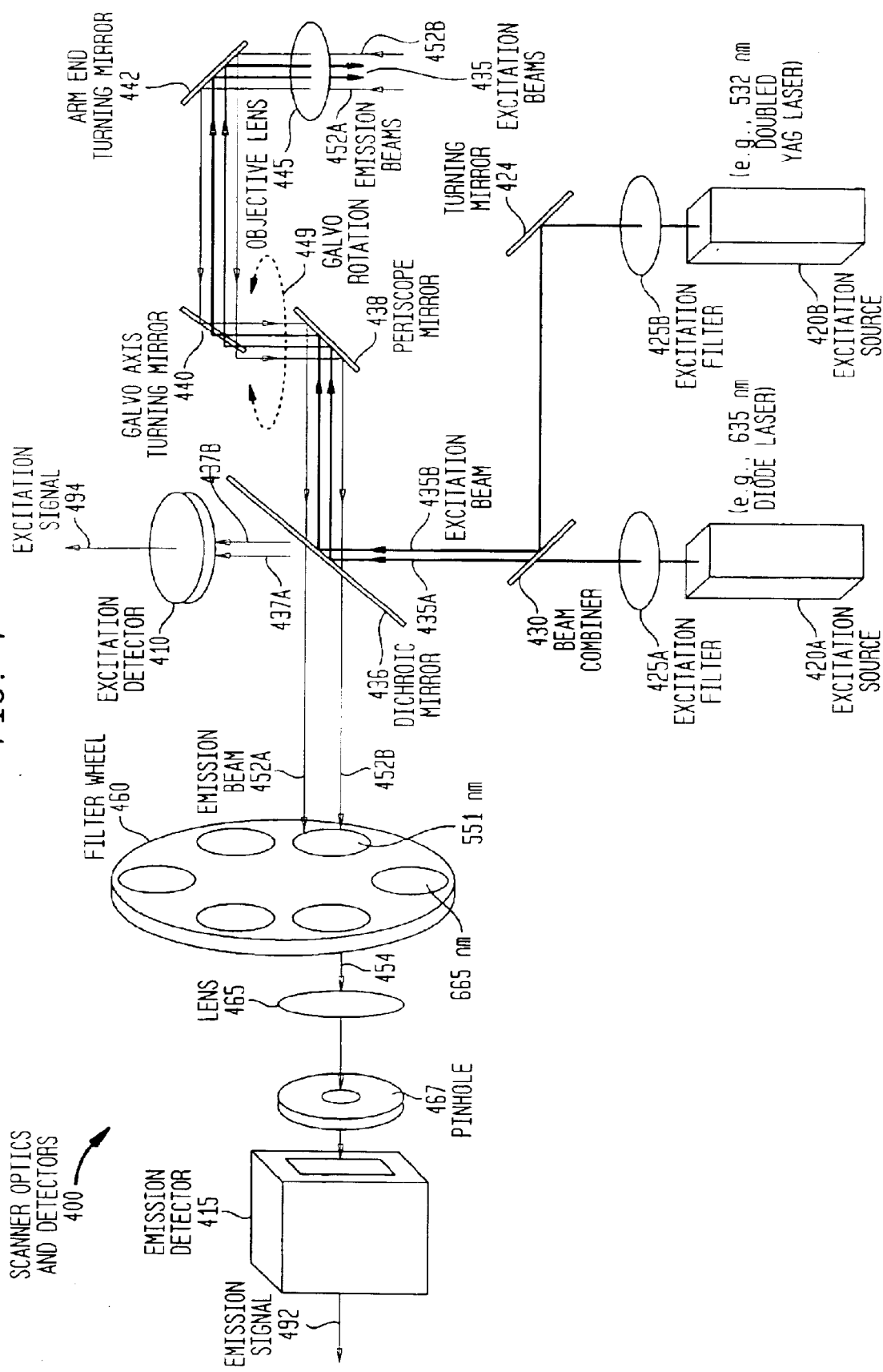
FIG. 4 is a simplified graphical representation of selected components of one embodiment of a scanner of FIG. 1 suitable for scanning arrays.

FIG. 4 is a simplified graphical representation of selected components of an illustrative type of scanner 160A suitable for scanning hybridized spotted arrays 132A and 132B disposed on slide 333 (i.e., in this example, spotted arrays 121A and 121B, respectively, after hybridization process 122). These illustrative components, which will be understood to be non-limiting and not exhaustive, are referred to collectively for convenience as scanner optics and detectors 400. Scanner optics and detectors 400 include excitation sources 420A and 420B (collectively referred to as excitation sources 420). Any number of one or more excitation sources 420 may be used in alternative embodiments. In the present example, sources 420 are lasers; in particular, source 420A is a diode laser producing red laser light having a wavelength of 635 nanometers and, source 420B is a doubled YAG laser producing green laser light having a wavelength of 532 nanometers. Further references herein to sources 420 generally will assume for illustrative purposes that they are lasers, but, as noted, other types of sources, e.g., x-ray sources, may be used in other implementations.

Sources 120A and 120B may alternate in generating their respective excitation beams 435A and 435B between successive scans, groups of successive scans, or between full scans of an array. Alternatively, both of sources 120 may be operational at the same time. For clarity, excitation beams 435A and 435B are shown as distinct from each other in FIG. 4. However, in practice, turning mirror 424 and/or other optical elements (not shown) typically are adjusted to provide that these beams follow the same path.

Scanner optics and detectors 400 also includes excitation filters 425A and 425B that optically filter beams from excitation sources 420A and 420B, respectively. The filtered excitation beams from sources 420A and 420B may be combined in accordance with any of a variety of known techniques. For example, one or more mirrors, such as turning mirror 424, may be used to direct filtered beam from source 420A through beam combiner 430. The filtered beam from source 420B is directed at an angle incident upon beam combiner 430 such that the beams combine in accordance with optical properties techniques well known to those of ordinary skill in the relevant art. Most of combined excitation beams 435 are reflected by dichroic mirror 436 and thence directed to periscope mirror 438 of the illustrative example. However, dichroic mirror 436 has characteristics selected so that portions of beams 435A and 435B, referred to respectively as partial excitation beams 437A and 437B and collectively as beams 437, pass through it so that they may be detected by excitation detector 410, thereby producing excitation signal 494.

Figure 5A:
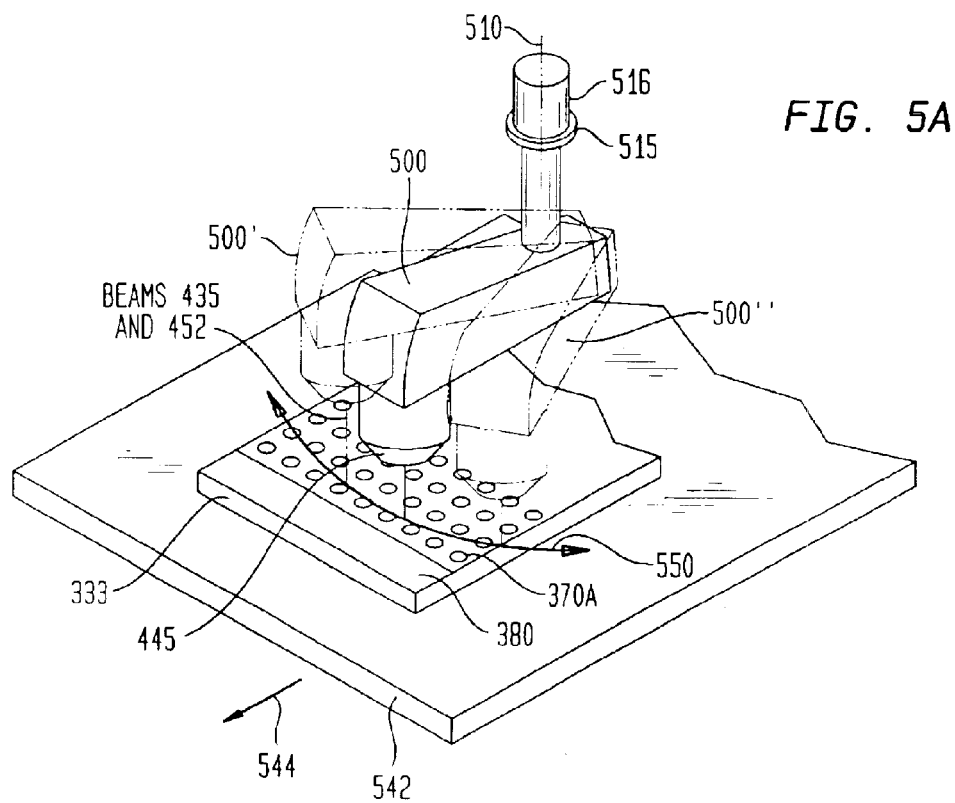
FIG. 5A is a perspective view of a simplified exemplary configuration of a scanning arm portion of the scanner of FIG. 4.
Figure 5B:
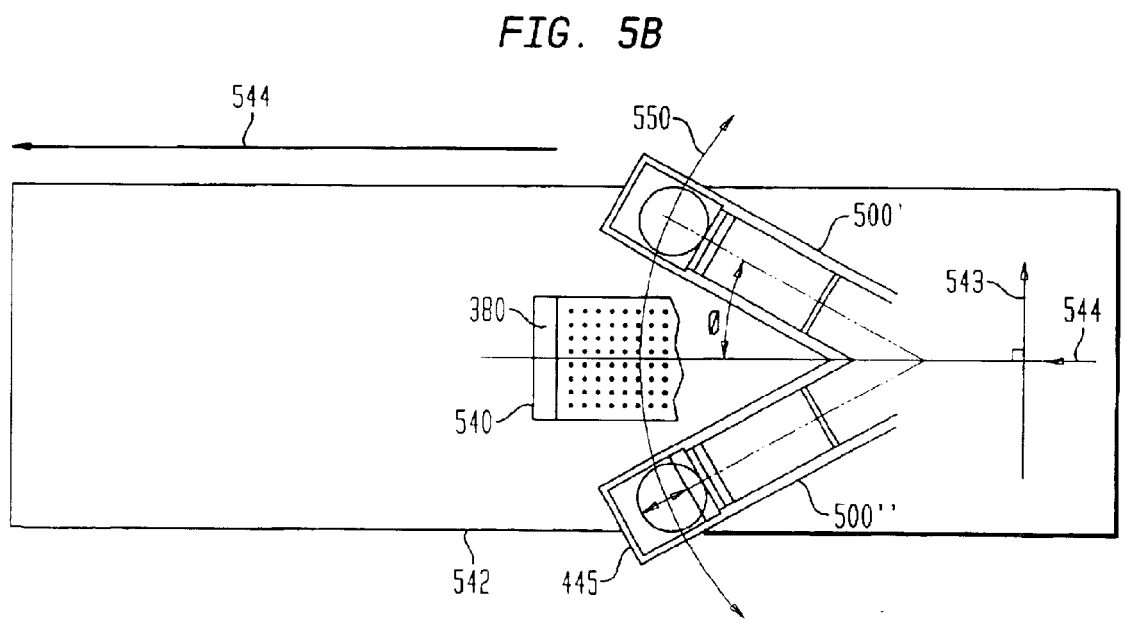
FIG. 5B is a top planar view of the scanning arm of FIG. 5A as it scans biological features on one embodiment of a spotted array being moved by a translation stage under the arm's arcuate path.

In the illustrated example, excitation beams 435 are directed via periscope mirror 438 and arm end turning mirror 442 to an objective lens 445. As shown in FIGS. 5A and 5B, lens 445 in the illustrated implementation is a small, lightweight lens located on the end of an arm that is driven by a galvanometer around an axis perpendicular to the plane represented by galvo rotation 449 shown in FIG. 4. Objective lens 445 thus, in the present example, moves in arcs over hybridized spotted arrays 132 disposed on slide 333. Flourophores in hybridized probe-target pairs of arrays 132 that have been excited by beams 435 emit emission beams 452 (beam 452A in response to excitation beam 435A, and beam 452B in response to excitation beam 435B) at characteristic wavelengths in accordance with well known principles. Emission beams 452 in the illustrated example follows the reverse path as described with respect to excitation beams 435 until reaching dichroic mirror 436. In accordance with well known techniques and principles, the characteristics of mirror 436 are selected so that beams 452 (or portions of them) pass through the mirror rather than being reflected.

In the illustrated implementation, filter wheel 460 is provided to filter out spectral components of emission beams 452 that are outside of the emission band of the fluorophore, thereby providing filtered beams 454. The emission band is determined by the characteristic emission frequencies of those fluorophores that are responsive to the frequencies of excitation beams 435. In accordance with techniques well known to those of ordinary skill in the relevant arts, including that of confocal microscopy, filtered beams 454 may be focused by various optical elements such as lens 465 and also passed through illustrative pinhole 467 or other element to limit the depth of field, and thence impinges upon emission detector 415.

Emission detector 415 may be a silicon detector for providing an electrical signal representative of detected light, or it may be a photodiode, a charge-coupled device, a photomultiplier tube, or any other detection device that is now available or that may be developed in the future for providing a signal indicative of detected light. For convenience of illustration, detector 415 will hereafter be assumed to be a photomultiplier tube (PMT). Detector 415 thus generates emission signal 492 that represents numbers of photons detected from filtered emission beam 454.

FIG. 5A is a perspective view of a simplified representation of the scanning arm portion of scanner optics and detectors 400. Arm 500 moves in arcs around axis 510, which is perpendicular to the plane of galvo rotation 449. A position transducer 515 is associated with galvanometer 515 that, in the illustrated implementation, moves arm 500 in bi-directional arcs. Transducer 515, in accordance with any of a variety of known techniques, provides an electrical signal indicative of the radial position of arm 500. Certain non-limiting implementations of position transducers for galvanometer-driven scanners are described in U.S. Pat. No. 6,218,803, which is hereby incorporated by reference in its entirety for all purposes. The signal from transducer 515 is provided in the illustrated implementation to user computer 100B so that clock pulses may be provided for digital sampling of emission signal 492 when arm 500 is in certain positions along its scanning arc.

Arm 500 is shown in alternative positions 500' and 500" as it moves back and forth in scanning arcs about axis 510. Excitation beams 435 pass through objective lens 445 on the end of arm 500 and excite fluorophore labels on targets hybridized to certain of probes 370 in arrays 132 disposed on slide 333, as described above. The arcuate path of excitation beams 435 is schematically shown for illustrative purposes as path 550. Emission beams 452 pass up through objective lens 445 as noted above. Slide 333 of this example is disposed on translation stage 542 that is moved in what is referred to herein as the y direction 544 so that arcuate path 550 repeatedly crosses the plane of arrays 132.

FIG. 5B is a top planar view of arm 500 with objective lens 445 scanning arrays 132 as translation stage 542 is moved under path 550. As shown in FIG. 5B, arcuate path 550 of this example is such that arm 500 has a radial displacement of θ in each direction from an axis parallel to direction 544. What is referred to herein as the x direction, perpendicular to y-direction 544, is shown in FIG. 5B as direction 543. Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030 and 6,201,639, all of which have been incorporated by reference above. It will be understood that although a galvanometer-driven, arcuate, scanner is described in this illustrative implementation, many other designs are possible, such as the voice-coil-driven scanner described in U.S. patent application Ser. No. 09/383,986, hereby incorporated herein by reference in its entirety for all purposes.

Figure 6A:
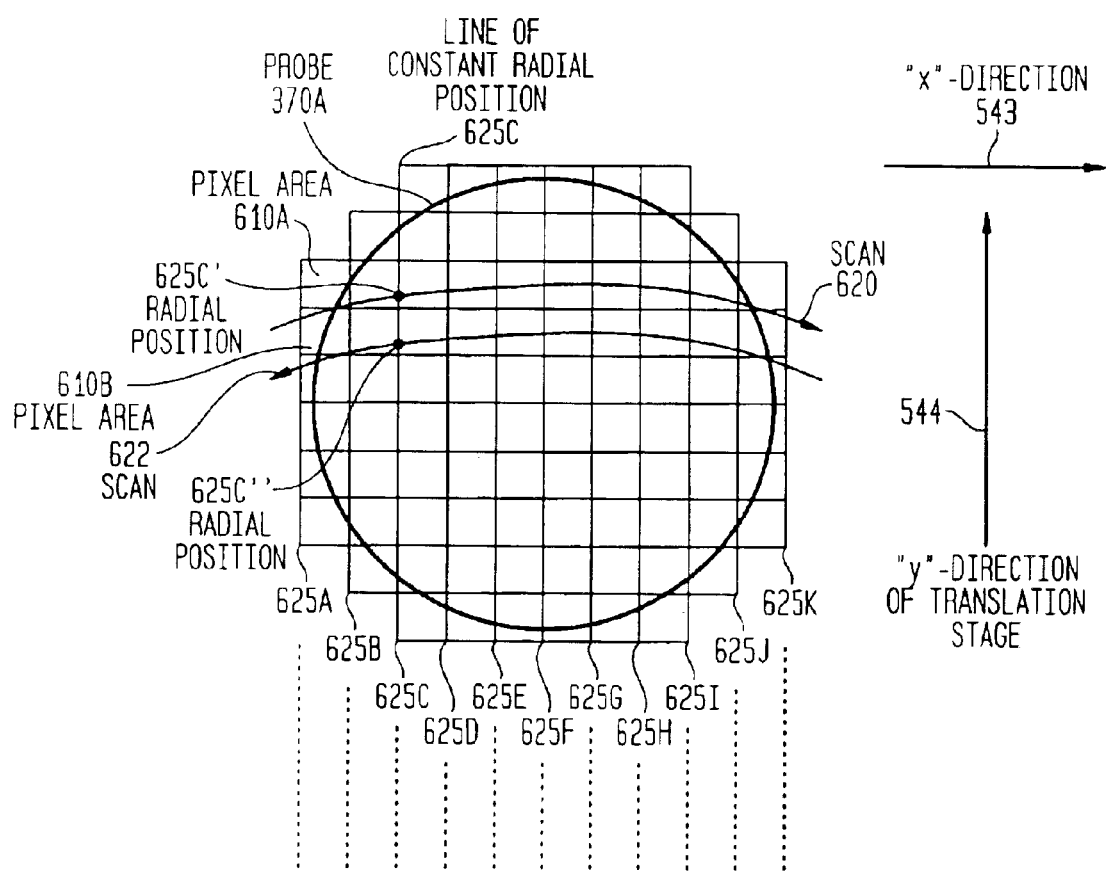
FIG. 6A is a graphical representation of one embodiment of a probe feature showing bi-directional scanning lines such as may be implemented using the scanning arm of FIGS. 5A and 5B.

FIG. 6A is a simplified graphical representation of illustrative probe 370A as it is scanned by scanner 160A. It is assumed for illustrative purposes that probe 370A has hybridized with a fluorescently labeled target. Although FIG. 6A shows probe 370A in idealized form, i.e. a perfect circle, it will be understood that many shapes, including irregular shapes, are possible.

In the manner described above, objective lens 445 scans over probe 370A (and other probes of arrays 132) in bi-directional arcs. An illustrative scan 620 is shown in FIG. 6A, which is not necessarily drawn to scale; e.g., the ratio of the radius of the arc of scan 620 to the radius of probe 370A is illustrative only. As also noted, probe 370A moves under objective lens 445 carried by translation stage 542 in y-direction 544. In particular, in the illustrated implementation, arm 500 scans in an arc in one direction, shown as left-to-right scan 620 in FIG. 6A. Translation stage 542 is then moved incrementally by a stepping motor (not shown) in y-direction 544 and arm 500 then scans back in the opposite direction, shown as right-to-left arcuate scan 622. Translation stage 542 is again moved in direction 544, and so on in scan-step-scan-step sequences. The distance between scans 620 and 622 thus corresponds to the distance that translation stage 542 is moved in each increment, although it will be understood that the distance shown in FIG. 6A is not necessarily to scale and is illustrative only. It will be understood that any other combination of scanning and stepping is possible in alternative implementations, and that scanning and moving of translation stage 542 may occur at the same or at overlapping times in some implementations. Translation stage 542 need not be stepped in some implementations, but may, for example, be moved continuously.

Figure 6B:
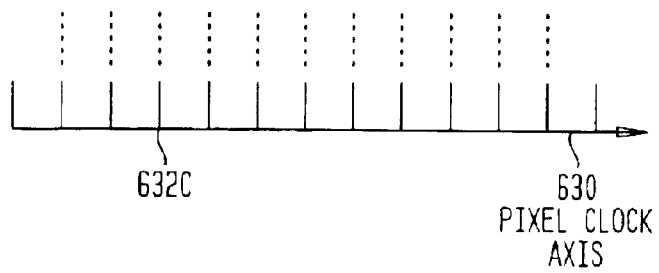
FIG. 6B is an illustrative plot of pixel clock pulses aligned with the scanned probe feature of FIG. 6A to show illustrative radial position sampling points.

FIG. 6B is a plot having a pixel clock axis 630 showing when clock pulses 632 occur. Clock pulses 632 may be generated by a pixel clock of scanner 160A (e.g., complex programmable logic device 830, described below) or, alternatively, they may be generated by software executing in computer 100B (e.g., executable 790', described below). Axis 630 in the illustrated implementation is a spatial axis; that is, each of clock pulses 632 occurs in reference to the radial location of arm 500 during each scan, as described in greater detail below. Thus, with reference to the position of translation stage 542 indicated by scan 620, a clock pulse 632A occurs prior to arm 500 passing over probe 370A from the left as shown in FIGS. 6A and 6B. (For sake of clarity of illustration only, vertical dotted lines are provided between FIGS. 6A and 6B, and between FIGS. 6B and 6C, to illustrate the alignment of these figures.) As another example, clock pulse 632C occurs with respect to scan 620 when arm 500 has just passed over portions of probe 370A indicated by pixel areas 610A and 610B. These areas are referred to as pixel areas because a digital value is assigned to each such area in the illustrated implementation based on the strength of a processed emission signal associated with that area. In accordance with known techniques, clock pulses 632 enable the digital sampling of the processed emission signal.

As noted, clock pulses 632 are spatially rather than temporally determined in the illustrated implementation. Moreover, in some aspects of the illustrated implementation, galvanometer 516 is driven by a control signal provided by user computer 100B such that the velocity of arm 500 in x-direction 444 is constant in time during those times when arm 500 is over probe 370A (and, typically, over other of probes 370 of arrays 132 as they are scanned). That is, dx/dt is a constant (and thus the angular velocity varies) over the probe-scanning portions of each arc and, in particular, it is a constant during the times when clock pulses are generated to enable digital sampling. As is evident, dx/dt must be reduced to zero between each successive scan, but this deceleration and reversal of direction takes place after arm 500 has passed over probe 370A (or, more generally, array 132A or 132B). The design and implementation of a galvanometer control signal to provide constant dx/dt are readily accomplished by those of ordinary skill in the relevant art.

Thus, the approximate sampling rate may readily be calculated based on the desired scanning speed (dx/dt) and desired pixel resolution. To provide an illustrative example, a spot deposited by an Affymetrix® 417™ or 427™ Arrayer typically has a diameter of approximately 150 to 200 microns. Spotted arrays made using these instruments typically may be deposited over a surface having a width of about 22 millimeters on a microscope slide that is 25 millimeters wide. In order to achieve pixel resolution of about 10 microns, a sampling rate of about 160 kHz is sufficient for scanning speeds typical for scanners used with respect to these probe arrays, such as the Affymetrix® 428™ scanner. Other sampling rates, readily determined by those of ordinary skill, may be used in other applications in which, for example, different scanning speeds are used and/or different pixel resolutions are desired. The desired pixel resolution typically is a function of the size of the probe features, the possibility of variation in detected fluorescence within a probe feature, and other factors.

User Computer 100B

Figure 7:
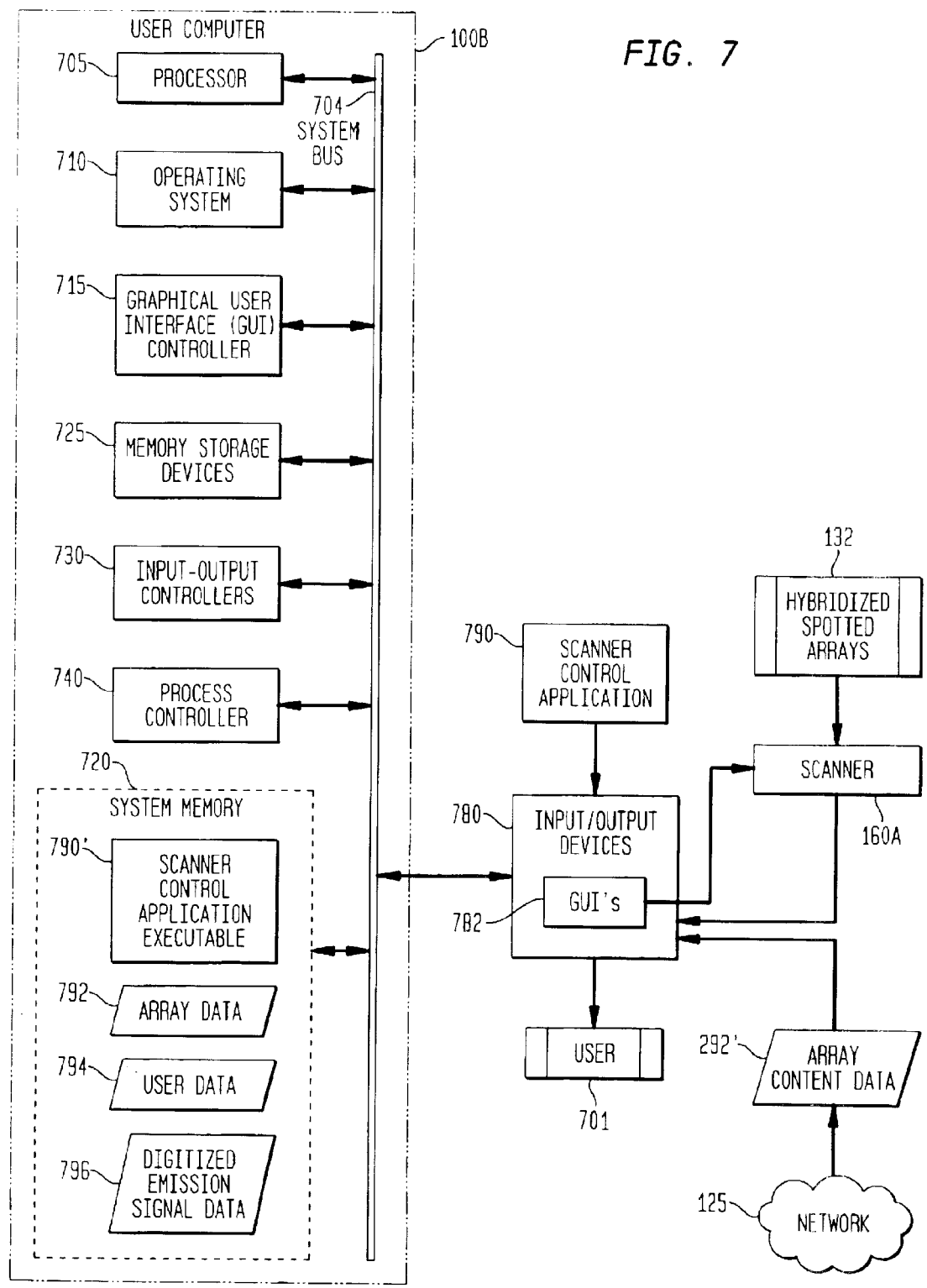
FIG. 7 is a functional block diagram of one embodiment of a scanner system of FIG. 1.

As shown in FIG. 1 and noted above, scanner 160B operates in the illustrated implementation under computer control, e.g., under the control of user computer 100B, as shown in greater detail in FIG. 7. Although computer 100B is shown in FIGS. 1 and 7 for clarity as being directly coupled to scanner 160A, it may alternatively be coupled to scanner 160A over a local-area, wide-area, or other network, including an intranet and/or the Internet. Computer 100B may be a personal computer, a workstation, a server, or any other type of computing platform now available or that may be developed in the future. Typically, computer 100B includes known components such as processor (e.g., CPU) 705, operating system 710, system memory 720, memory storage devices 725, GUI controller 715, and input-output controllers 730, all of which typically communicate in accordance with known techniques such as via system bus 704. It will be understood by those skilled in the relevant art that there are many possible configurations of the components of computer 100B and that some components that may typically be included in computer 100B are not shown, such as cache memory, a data backup unit, and many other devices.

Input-output controllers 730 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 730 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 715 may comprise any of a variety of known or future software programs for providing graphical input and output interfaces between computer 100B and a user 701 (e.g., an experimenter wishing to use scanner 160A to acquire and analyze information from spotted arrays), and for processing inputs from user 701 (hereafter sometimes referred to as user inputs or user selections). To avoid confusion, references hereafter to a GUI generally are directed to one or more graphical user interfaces displayed on a display device of devices 780 to user 701, such as GUI 782A of FIGS. 8 and 9, described below. To be distinguished are references to a GUI controller, such as GUI controller 715, that operates to display the GUI's to user 701 and to process input information provided by user 701 through the GUI's. As is well known in the relevant art, a user may provide input information using a GUI by selecting, pointing, typing, speaking, and/or otherwise operating, or providing information into, one or more input devices of devices 780 in a known manner.

Computer 100B may optionally include process controller 740 that may, for example, be any of a variety of PC-based digital signal processing (DSP) controller boards, such as the M44 DSP Board made by Innovative Integration of Simi Valley, Calif. More generally, controller 740 may be implemented in software, hardware or firmware, or any combination thereof.

Scanner Control and Analysis Application 790

Scanner control application 790 of the illustrated implementation is a software application that controls functions of scanner 160A. In addition, when executed in coordination with processor 705, operating system 710, GUI controller 715, and/or process controller 740, application 790 performs user interface functions, data and image processing operations, and data transfer and storage operations related to data provided by or to scanner 160A and/or user 701, as described in greater detail below. Affymetrix® Jaguar™ software, available from Affymetrix, Inc., is a commercial product that, in some implementations, includes various aspects of application 790.

Figure 8:
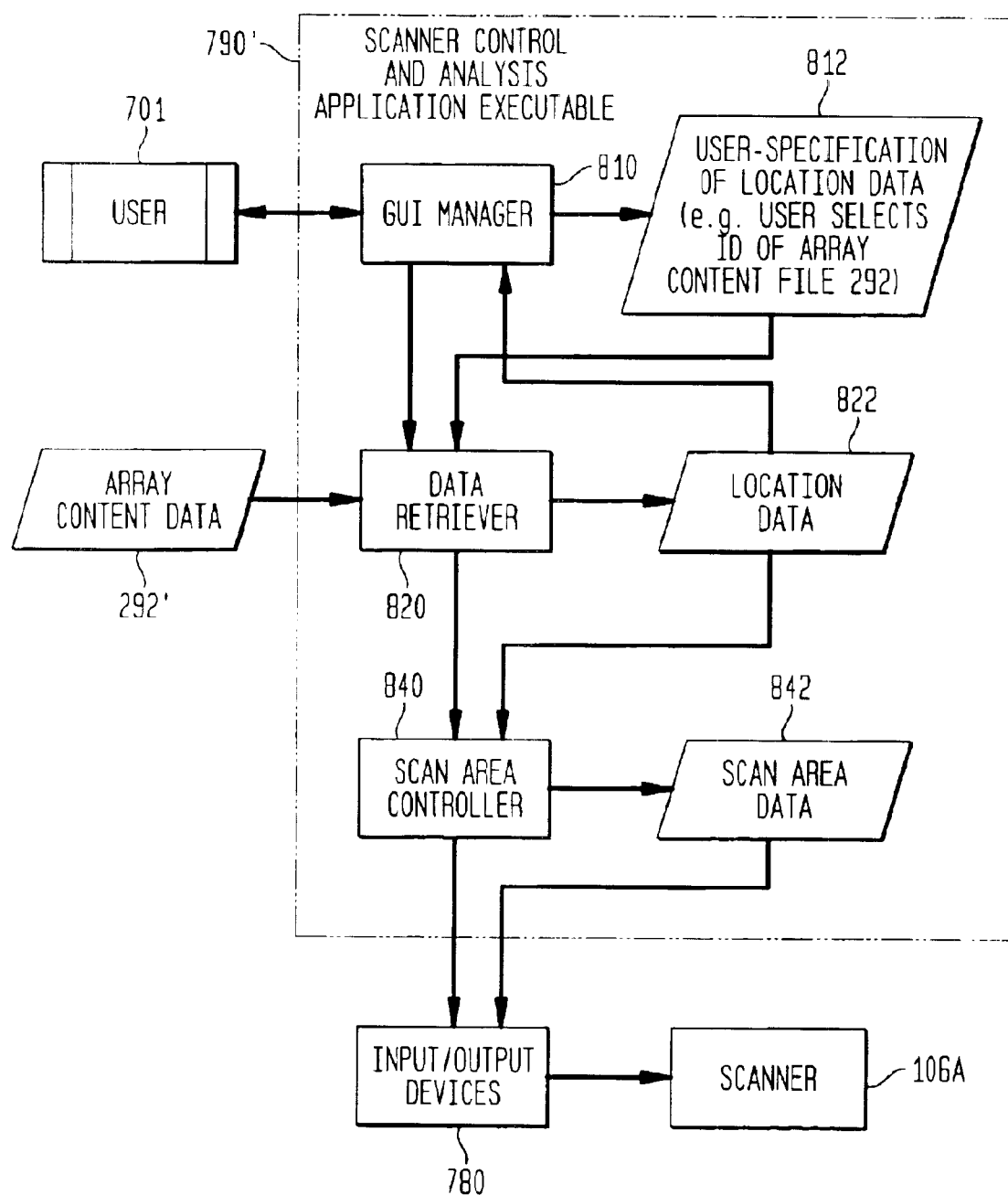
FIG. 8 is functional block diagram of one embodiment of a scanner control and analysis application (i.e., computer program product)

More particularly as shown in FIG. 8, scanner control application 790 in the illustrated implementation includes a GUI manager 810 that enables user 701 to specify a file (or other data structure in other implementations) including location data corresponding to probe-feature locations on a substrate to be scanned. Also included in application 790 is data retriever 820 that, based on the selection made by user 701, accesses the location data and provides this data to another element of application 790, scan area controller 840. Scan area controller 840 controls scanner 160A so that its scanning area includes a scanning area within which the probe-feature locations specified by the location data are located. These operations are now further described and their relations to method steps of the illustrative flow chart of FIG. 11 are parenthetically indicated.

Figure 9:
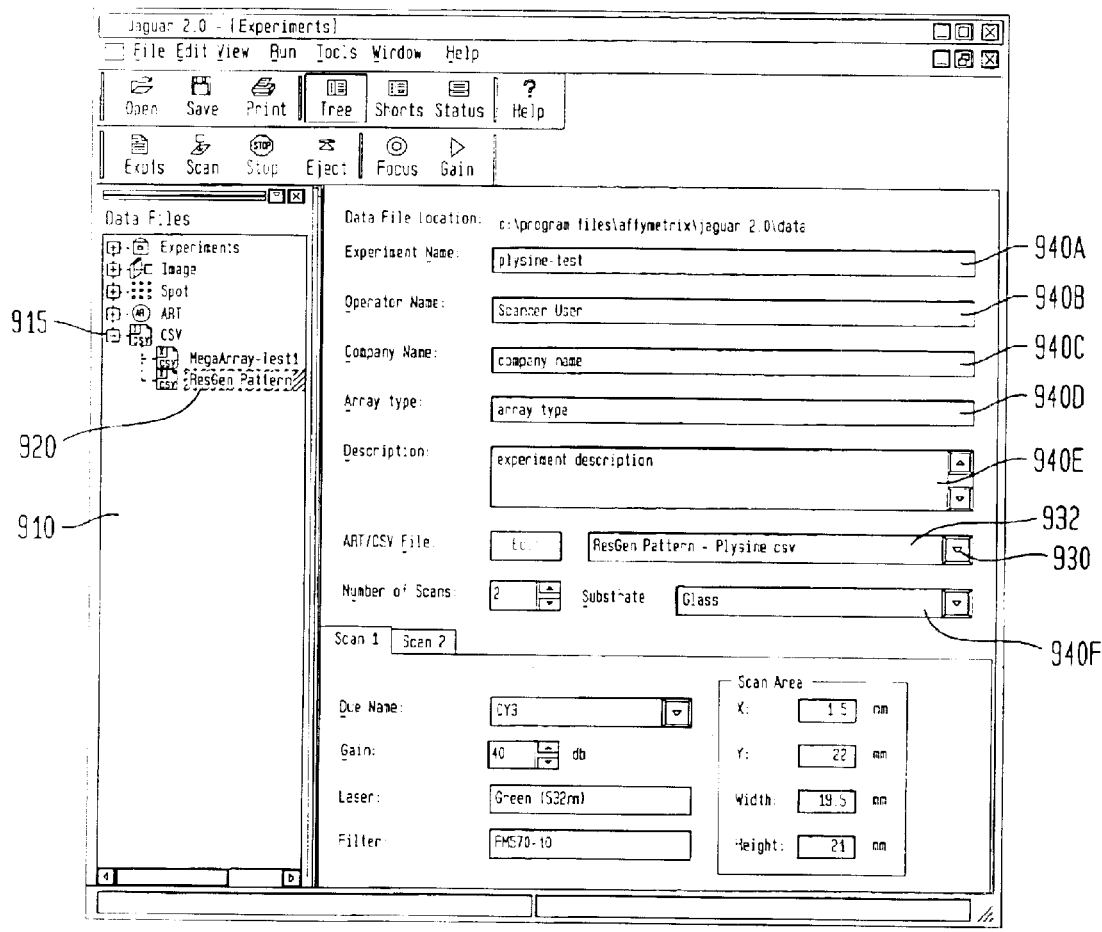
FIG. 9 is an illustrative implementation of a graphical user interface employed in cooperation with the application of FIG. 8 to retrieve probe-feature location data.
Figure 11:
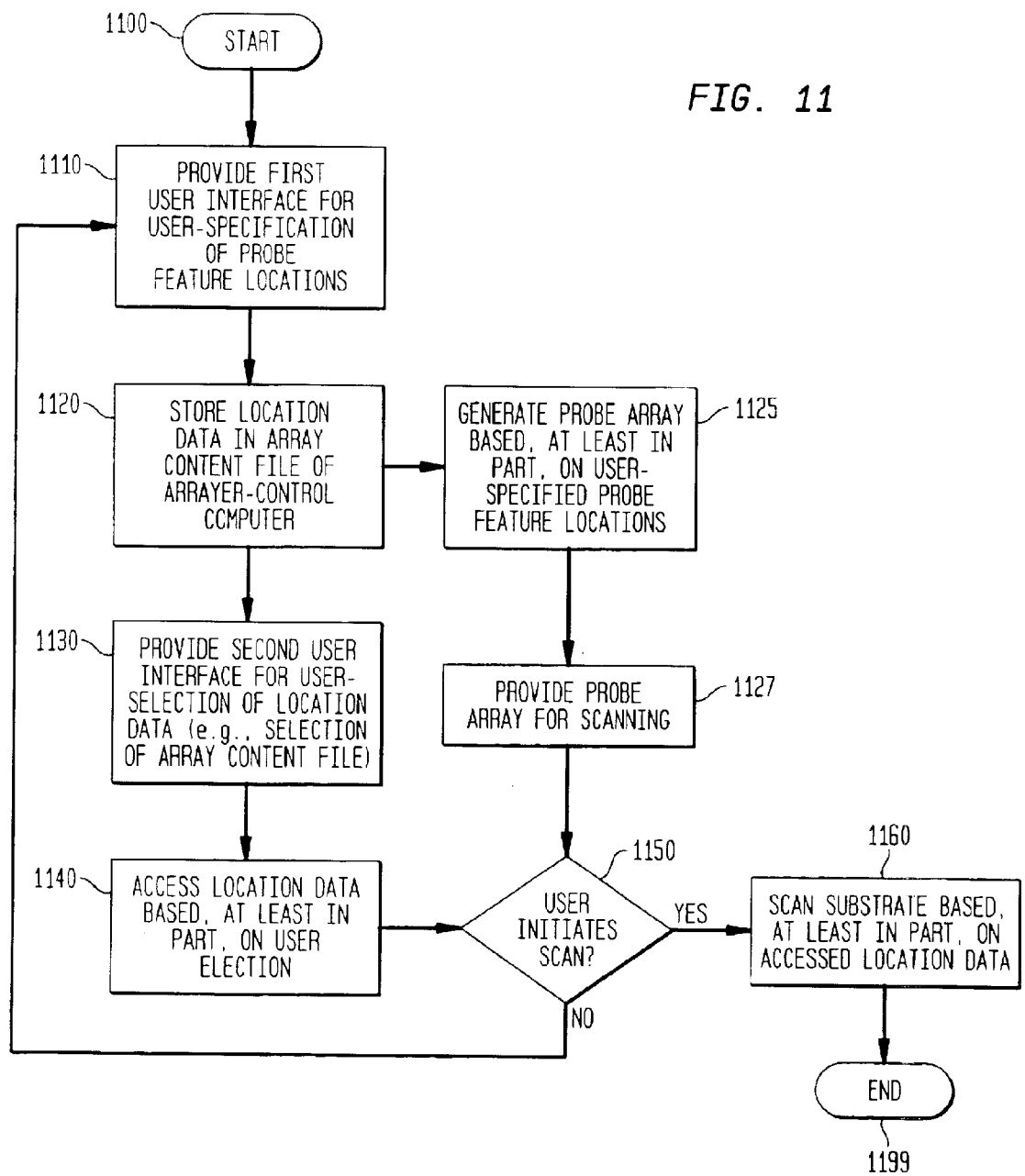
FIG. 11 is a flow diagram showing steps implemented by illustrative embodiments of the application of FIG. 8 and an illustrative arrayer manager application of FIG. 2.

In connection with FIGS. 2 and 3A, it was noted above that user 201 may specify probe feature locations in a variety of ways (see corresponding illustrative method step 1110 in FIG. 11). These selections, as also noted, may be stored in computer 100A as an array content file (or other data structure) such as illustrative file 292 (see step 1120). GUI manager 810, in cooperation with GUI controller 715 noted above, receives user selections of file identifiers in an illustrative implementation from user 701 through GUI 782A as shown in FIG. 9 (see step 1130). GUI 782A includes a file tree window 910 in which user 701 may select from a list of csv files that, in this example, are array content files (such as file 292) identified by a .csv file extension. In particular, it is illustratively assumed that user 701 selects array content file 920 from expandable-collapsible csv node 915. Alternatively, user 701 may make this selection in accordance with any of a variety of other conventional techniques, such as selecting an item from a pull down list using graphical elements 930 and 932. GUI manager 810, in accordance with conventional techniques, thus provides to data retriever 820 user 701's specification of location data 812 for use in scanning a substrate specified, for example, in one or more of graphical elements 940A–F.

Figure 10:
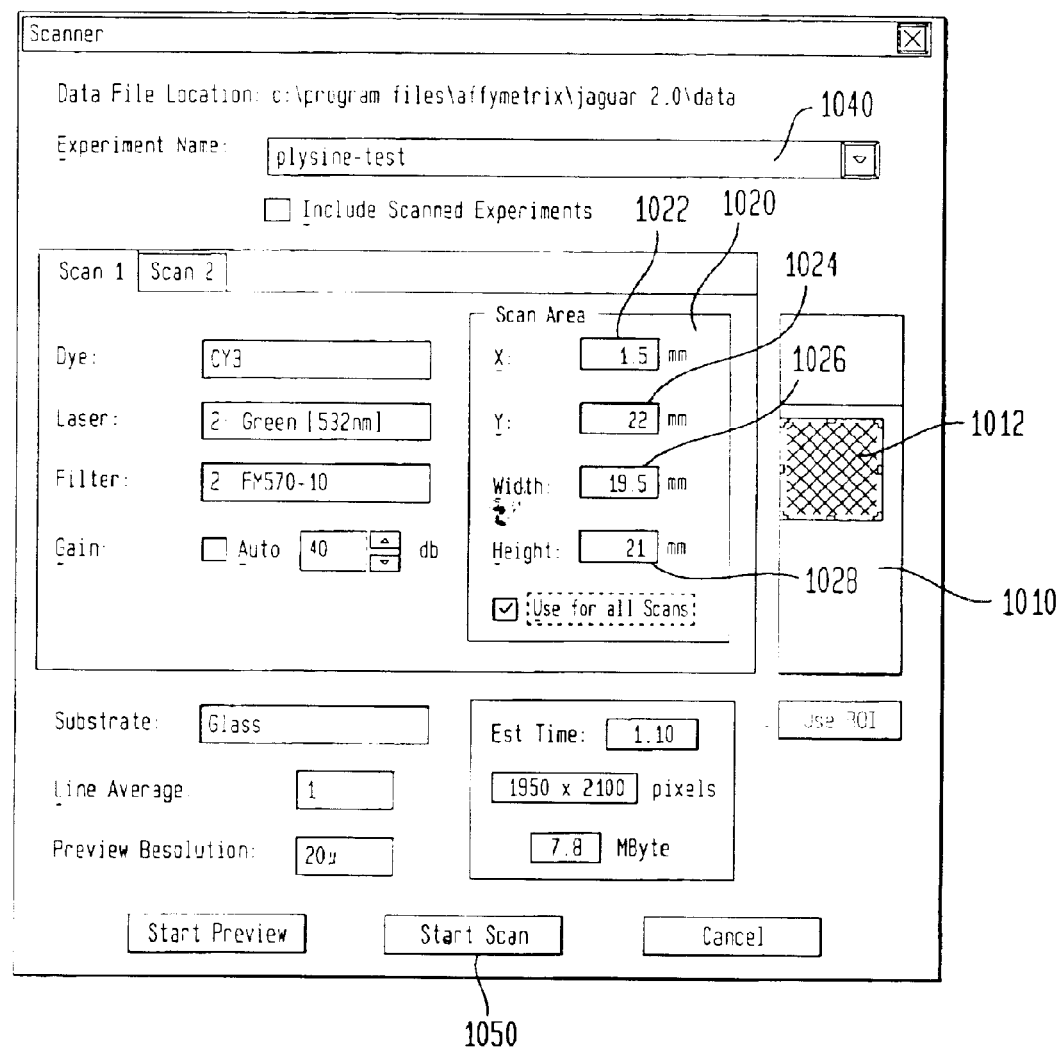
FIG. 10 is an illustrative implementation of another graphical user interface employed in cooperation with the application of FIG. 8 to retrieve probe-feature location data.

Employing any of a variety of conventional techniques for retrieving data over a network or otherwise, data retriever 820 retrieves array content data 292' and, in this implementation, stores it in array data file 792 in system memory 720 of computer 100B, as shown in FIG. 7. In particular, data retriever 820 may extract probe location data from array data 792, as illustrated by location data 822 of FIG. 8 (see step 1140). Data retriever 820 in this example provides this data to scan area controller 840 and, in some implementations, to GUI manager 810. Using this data, GUI manager 810 may advantageously display to user 701 the probe location information obtained by data retriever 820. For example, GUI 782B of FIG. 10 includes scan area display window 1010 and scan area data window 1020. Included in window 1020 are x and y coordinate information as extracted from array data 792 showing, for example, user-selected reference x and y coordinates 1022 and 1024. Illustratively assuming that user 701 had selected a spacing between probe locations, as discussed above, then the these coordinates 1022 and 1024 establish probe locations for probes in the array or arrays identified by graphical element 940A of GUI 782A and corresponding graphical element 1040 of GUI 782B. In the example illustrated in FIG. 10, user 701 may change the scan area by changing coordinates 1022 and/or 1024, perhaps based on viewing a representation of the scan area 1012 as displayed in window 1010. User 701 may also change the scan area by changing the values for scan area width 1026 and/or scan area height 1028 in window 1020, and/or by dragging buttons provided on the representation of scan area 1012, all in accordance with conventional techniques.

User 701 may initiate a scan that includes scan area 1012 in accordance with any of a variety of conventional techniques, such as by selecting start scan button 1050 (see decision element 1150 and step 1160). Upon receiving this command, scan area controller 840 initiates scanning by scanner 160A, typically through output devices of input/output devices 780, in accordance with conventional techniques. In some implementations, controller 840 may cause repeated scans to be made on each of two or more different substrates using probe location data extracted from one or more user-selected array content files. For example, user 701 may specify two or more array content files 292, as by selecting multiple files from node 915. Controller 840 then may initiate batch scans, in serial or parallel, using one or more scanners 160, of multiple slides or other substrates using the location data contained in the user-selected array content files.

As will be evident to those skilled in the relevant art, application 790 may be loaded into system memory 720 and/or memory storage device 725 through an input device of devices 780. Alternatively, application 790 may be implemented as executable instructions stored in firmware, or a combination of firmware and software. Executable code corresponding to application 790 is referred to as scanner control application executable 790' and is shown for convenience with respect to the illustrated implementation as stored in system memory 720. However, instructions and data including executable instructions of executable 790', and data used or generated by it, may be located in or shifted among other memory devices, local or remote, as convenient for data storage, data retrieval, and/or execution. The instructions of executable 790', also called computer control logic, when executed by processor 705, enable computer 100B to perform functions of the illustrated systems. Accordingly, executable 790' may be referred to as a controller of computer 100B. More specifically, in some implementations, the present invention includes a computer program product comprising a computer usable medium having control logic (computer software program, including program code) stored therein. In various embodiments, software products may be implemented using any of a variety of programming languages, such as Visual C++ or Visual Basic from Microsoft Corporation, Java™ from Sun Microsystems, Inc., and/or other high or lower level programming languages. The control logic, when executed by processor 705, causes processor 705 to perform some of the functions of the invention, as described herein. In other embodiments, some functions of the present invention may be implemented primarily in hardware using, for example, a hardware state machine. Implementation of the hardware state machine so as to perform the functions described herein will be apparent to those skilled in the relevant arts.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

For example, arrayer manager application 290 is described as executing on computer 100A that controls arrayer 120, and scanner control application 790 is described as executing on computer 100B that control scanner 160A. However, aspects of the invention need not be divided into these distinct functional elements. Rather, for example, applications 290 and 790 could be executed on a same computer that may, for example, control both arrayer 120 and scanner 160A. Moreover, applications 290 and 790 may be part of a same computer program product irrespective of whether they are executed on a same, or different, computers. Similarly, operations of a particular functional element that are described separately for convenience need not be carried out separately. Similarly, in some embodiments, any functional element may perform fewer, or different, operations than those described with respect to the illustrated embodiment. Also, functional elements shown as distinct for purposes of illustration may be incorporated within other functional elements in a particular implementation.

Also, the sequencing of functions or portions of functions generally may be altered. For example, the method steps shown in FIG. 11 generally need not be carried out in the order suggested by this figure. Among many possible examples, steps 1130 and 1140 could be combined or carried out in parallel, steps 1130 and 1140 could be carried out after steps 1125 and 1127, and so on.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel processing or for other reasons. Also, intermediate data structures or files may be used, various described data structures or files may be combined, the sequencing of functions or portions of functions generally may be altered, and so on. Numerous other embodiments, and modifications thereof, are contemplated as falling within the scope of the present invention as defined by appended claims and equivalents thereto.

What is claimed is:

1. A method comprising the steps of:
   (a) receiving data corresponding to a plurality of probe locations on a substrate;
   (b) storing the data;
   (c) providing a first user interface that enables user selection of the data;
   (d) accessing the data based, at least in part, on the user selection; and
   (e) scanning the substrate based, at least in part, on the accessed data.

2. The method of claim 1, further comprising:
   (f) providing a second user interface that enables user specification of the probe locations.

3. The method of claim 2, wherein;
the second user interface enables user specification of the probe locations by specifying one or more spacing distances between probes.

4. The method of claim 2, wherein:
the second user interface enables user specification of the one or more probe locations by specifying one or more patterns of probe locations.

5. The method of claim 2, wherein:
the second user interface enables user specification of the one or more probe locations by specifying coordinates.

6. The method of claim 5, wherein:
the coordinates include x and y coordinates.

7. The method of claim 5, wherein:
the coordinates include user-specified coordinates of a reference point on the substrate.

8. The method of claim 5, wherein:
the coordinates include user-specified coordinates of one or more probe locations on the substrate.

9. The method of claim 1, wherein:
the data is received from memory of a first computer by memory of a second computer; and
the data is accessed from the memory of the second computer.

10. The method of claim 9, wherein:
the second computer is constructed and adapted to control a scanner.

11. The method of claim 1, wherein:
the probe locations include locations of probes of a spotted array.

12. The method of claim 1, wherein:
the probe locations include locations of probes of a synthesized array.

13. A computer program product, comprising:
(a) a user-interface manager that
 (i) enables user specification of a plurality of probe locations on a substrate, wherein the user-interface manager enables user specification of the probe locations by specifying from the group consisting of one or more spacing distances between probes, one or more patterns of probe locations, and one or more probe locations by specifying coordinates, and
 (ii) provides data corresponding to the probe locations;
(b) a data storage manager that stores the data in memory; and
(c) an output manager enabled to provide the data to a scanner control application constructed and arranged to cause scanning of the substrate based, at least in part, on the accessed data.

14. The computer program product of claim 13, wherein:
the coordinates include x and y coordinates.

15. The computer program product of claim 13, wherein:
the coordinates include user-specified coordinates of a reference point on the substrate.

16. The computer program product of claim 13, wherein:
the coordinates include user-specified coordinates of one or more probe locations on the substrate.

17. A computer program product, comprising:
(a) a data retriever that provides a user interface that enables a user selection of data corresponding to a plurality of probe locations on a substrate and accesses the data based, at least in part, on the user selection, wherein the data retriever receives the data from memory of a first computer and stores the data in memory of a second computer; and
(b) a scan-area controller that controls scanning of the substrate based, at least in part, on the accessed data.

18. The computer program product of claim 17, wherein:
the first computer is constructed and adapted to control an arrayer.

19. The computer program product of claim 17, wherein:
the second computer is constructed and adapted to control a scanner.

20. The computer program product of claim 17, wherein:
the probe locations include locations of probes of a spotted array.

21. The computer program product of claim 17, wherein:
the probe locations include locations of probes of a synthesized array.

22. A scanning system, comprising:
(a) a scanner; and
(b) a computer program product, comprising
 (i) a data retriever that provides a user interface that enables a user selection of data corresponding to a plurality of probe locations on a substrate and accesses the data based, at least in part, on the user selection, wherein the data retriever receives the data from memory of a first computer and stores the data in memory of a second computer, and
 (ii) a scan-area controller that controls scanning by the scanner of the substrate based, at least in part, on the accessed data.

23. A scanning system, comprising:
(a) a computer;
(b) a scanner, and
(c) a computer program product that, when executed on the first computer, performs a method comprising the steps of
 (i) receiving data corresponding to a plurality of probe locations on a substrate,
 (ii) storing the data,
 (iii) providing a user interface that enables a user selection of the data corresponding to a plurality of probe locations on a substrate,
 (iv) accessing the data based, at least in part, on the user selection, and
 (v) controlling scanning by the scanner of the substrate based, at least in part, on the accessed data.

* * * * *